United States Patent
Chevalier et al.

(10) Patent No.: US 6,361,782 B1
(45) Date of Patent: Mar. 26, 2002

(54) COSMETIC COMPOSITION IN ANHYDROUS FORM COMPRISING A DISPERSION OF A SURFACE-STABILIZED POLYMER PARTICLES

(75) Inventors: Veronique Chevalier, Villecresnes; Valerie Hurel, Gif/S/Yvette, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/551,629

(22) Filed: Apr. 17, 2000

(30) Foreign Application Priority Data

Apr. 16, 1999 (FR) .............................................. 99 04815

(51) Int. Cl.$^7$ ........................... A61K 7/00; A61K 31/74
(52) U.S. Cl. ..................... 424/401; 424/78.02; 424/63; 514/844; 514/845
(58) Field of Search ................................ 424/78.02, 59, 424/69, 70.12, 401, 63

(56) References Cited

U.S. PATENT DOCUMENTS 5,945,095 A * 8/1999 Mougin et al. .......... 424/78.02

FOREIGN PATENT DOCUMENTS

| EP | 0 400 546 A | 12/1990 |
| EP | 0 504 066 A | 9/1992 |
| EP | 0 797 976 A2 | 10/1997 |
| FR | WO 94/13628 | 6/1994 |
| FR | WO 97/01321 | 1/1997 |

* cited by examiner

*Primary Examiner*—Diana Dudash
*Assistant Examiner*—Gina Yu
(74) *Attorney, Agent, or Firm*—Oblon, Spivak, McClelland, Maier & Neustadt, P.C.

(57) ABSTRACT

The present invention relates to a composition, in particular a cosmetic or dermatological composition, for caring for and/or making up the skin, that includes:

a liquid fatty phase including polymer particles that are dispersed and surface-stabilized therein, and a dyestuff, wherein the liquid fatty phase includes a volatile liquid phase and a non-volatile liquid phase, the non-volatile phase having a solubility parameter $\delta_h \leq 5$ $(J/cm^3)^{1/2}$ and wherein a volatile phase/non-volatile phase weight ratio ranges from 2 to 25. This composition makes it possible to obtain on the skin a flexible, comfortable, non-greasy film which can camouflage marks, dyschromia and couperose on the skin. The invention also relates to a process for camouflaging marks and other dyschromia on the skin.

23 Claims, No Drawings

COSMETIC COMPOSITION IN ANHYDROUS FORM COMPRISING A DISPERSION OF A SURFACE-STABILIZED POLYMER PARTICLES

BACKGROUND OF THE INVENTION

1. Field of the Invention

The present invention relates to a composition in anhydrous form for caring for and/or making up the skin of both the human face and body, containing polymer particles which are dispersible in a fatty phase and a dyestuff. This composition is especially suitable for cosmetics and dermatology, and in particular allows the camouflaging of marks (vitiligo), skin pigmentation defects, dyschromia (angiomas) and couperose. This composition also has noteworthy water-resistance and transfer-resistance properties.

This composition can be in particular in the form of a paste, a gel or a cream which is more or less fluid and can be a foundation, a tinted skincare composition, an antisun composition, a composition for artificially tanning the skin or a make-up composition for the body, or alternatively an eyeshadow, a face powder or a concealer product.

2. Discussion of the Background

To camouflage marks, in particular age marks, due to impaired melanogenesis, skin pigmentation defects, dyschromia, couperose, diffuse irrigations (appearance of small blood vessels under the skin) and telangiectasia, foundations with high covering power are generally used. These foundations generally contain fatty phases such as waxes and oils, pigments and/or fillers and, optionally, additives such as cosmetic or dermatological active agents.

They can also contain "pasty" products having a soft consistency, thus making it possible to obtain colored pastes to be applied with a brush, the fingers or a sponge.

When are applied to the skin, these compositions have the drawback of transferring, i.e. of becoming at least partly deposited or leaving marks on certain supports with which they may come into contact such as the clothing or the skin. This results in mediocre persistence of the film applied, making it necessary to freshen the application of the foundation composition regularly. Moreover, the appearance of these unacceptable marks in particular on shirt collars may put certain women off using this type of product.

EP-A-709 083 describes foundations containing volatile silicones and a silicone resin having a three-dimensional structure, which have "transfer-resistance" properties. Unfortunately, after the silicone oils evaporate, these foundations have the drawback of leaving a film on the skin, which becomes uncomfortable over time (sensation of drying out and of tautness), which may put certain women off products of this type. To improve the level of comfort of these products, non-volatile silicone or non-silicone oils may be added thereto, but, in this specific case, the "transfer-resistance" efficacy would be lost.

More recently, EP-A-775 483 has envisaged skin compositions in the form of an aqueous dispersion of film-forming polymer. These compositions have good "transfer-reference" and water-resistance properties. Unfortunately, after the water evaporates, these films have the drawback of being uncomfortable over time.

At the present time, there is no simple and long-lasting means for hiding marks on the hands and the body of human beings, which does not mark clothing and which is resistant to water, sweat and sebum.

A need thus exists for a composition that does not have the above drawbacks, and in particular has properties of camouflaging the marks and other dyschromias on the skin and diffuse blood irrigations, and which is long-lasting, while at the same time having noteworthy "transfer-resistance" properties, even under pronounced pressure or rubbing, and which does not dry out the skin onto which it is applied, either during application or over time.

SUMMARY OF THE INVENTION

Accordingly, it is an object of the present invention to provide a composition that does not have the above-described drawbacks.

It is another object of the present invention to provide a composition that has the properties of camouflaging the marks and other dyschromias on the skin and diffuse blood irrigations.

It is another object of the present invention to provide a composition that is long-lasting.

It is another object of the present invention to provide a composition that has noteworthy "transfer-resistance" properties, even under pronounced pressure or rubbing.

It is another object of the present invention to provide a composition that does not dry out the skin onto which it is applied, either during application or over time.

These and other objects of the invention have been attained by the present invention, the first embodiment of which provides an anhydrous composition for the skin, including:

a liquid fatty phase including polymer particles that are dispersed and surface-stabilized therein, and a dyestuff, wherein the liquid fatty phase includes a volatile liquid phase and a non-volatile liquid phase, the non-volatile phase having a solubility parameter $\delta_h \leq 5$ $(J/cm^3)^{1/2}$ and wherein a volatile phase/non-volatile phase weight ratio ranges from 2 to 25.

Another embodiment of the present invention provides a method of reducing or eliminating eliminate marks, dyschromia, pigmentation defects, couperose and/or diffuse blood irrigations appearing across the skin, that includes applying to the skin an anhydrous composition for the skin, including:

a liquid fatty phase including polymer particles that are dispersed and surface-stabilized therein, and a dyestuff, wherein the liquid fatty phase includes a volatile liquid phase and a non-volatile liquid phase, the non-volatile phase having a solubility parameter $\delta_h \leq 5$ $(J/cm^3)^{1/2}$ and wherein a volatile phase/non-volatile phase weight ratio ranges from 2 to 25.

Another embodiment of the invention provides a non-therapeutic or cosmetic process for the camouflaging and/or the remanent camouflaging of marks, skin pigmentation defects, dyschromia, couperose, diff-use blood irrigations appearing across the skin and telangiectasias, including applying to the skin an anhydrous composition for the skin, including:

a liquid fatty phase including polymer particles that are dispersed and surface-stabilized therein, and a dyestuff, wherein the liquid fatty phase includes a volatile liquid phase and a non-volatile liquid phase, the non-volatile phase having a solubility parameter $\delta_h \leq 5$ $(J/cm^3)^{1/2}$ and wherein a volatile phase/non-volatile phase weight ratio ranges from 2 to 25.

By use of the present invention, it is possible to obtain a cosmetic or dermatological composition which gives a covering and camouflaging cohesive deposit, which has very good staying power, does not transfer at all and is resistant to water, sweat and sebum, while at the same time being very pleasant to apply and to wear throughout the day. In particular, the deposit is not greasy or dry, and is flexible and non-sticky.

DETAILED DESCRIPTION OF THE INVENTION

Various other objects, features and attendant advantages of the present invention will be more fully appreciated as the same becomes better understood from the following detailed description of the preferred embodiments of the invention.

The expression "liquid fatty phase" preferably means any non-aqueous medium which is liquid at room temperature (25° C.) and atmospheric pressure (760 mmHg). The expression "volatile liquid phase" preferably means any non-aqueous medium which can evaporate on contact with the skin in less than an hour, at room temperature and atmospheric pressure. This volatile phase preferably includes oils having a non-zero vapor pressure, at room temperature and atmospheric pressure, ranging more preferably from $10^{-3}$ to 300 mmHg (0.13 Pa to 40,000 Pa), and most preferably $10^{-2}$ to 100 mmHg. These ranges include all values and subranges therebetween. The liquid phase which does not correspond to this last definition is a nonvolatile liquid phase.

For a volatile phase/non-volatile phase weight ratio, this ratio being denoted as R, of less than 2, a film is obtained on the skin which does not dry, feels tacky and transfers. The camouflaging is thus not remanent. For a ratio R of greater than 25, a film is obtained which dries much too quickly, leading to the formation of a powder which does not adhere to the skin. Preferably, R is chosen in the range from 5 to 15, and more preferably from 7 to 12.5. These ranges include all values and subranges therebetween.

This composition is preferably a cosmetic or dermatological composition. It may thus contain ingredients that are compatible with the skin.

In addition to the advantages mentioned above, this composition may be transparent (i.e. it may produce a natural make-up effect), capable of homogenizing the skin color instantaneously and durably (for about a day, even if washed). The film obtained also has the advantage of being easy to remove with a conventional make-up remover (make-up-removing lotion or milk). Moreover, these compositions are very stable: no decantation and/or phase separation after 2 months at 45° C. and after 3 years at room temperature.

The composition of the invention is especially suited to caring for and protecting the hands.

The amount of polymer should be sufficient to form on the skin of the face and/or body, including the neck, the feet and the hands, a film capable of trapping the dyestuffs in order to limit, or even eliminate, their transfer onto a support with which the film is placed in contact. The amount of polymer preferably depends on the amount of dyestuffs contained in the composition. Preferably, the amount of polymer is greater than 2% by weight (as active material), relative to the total weight of the composition, more preferably greater than 5% by weight, and most preferably greater than 10% by weight. These ranges include all values and subranges therebetween. Preferably, the polymer is in the form of particles.

Another preferred embodiment of the invention is the use, in a cosmetic composition or for the manufacture of a physiologically acceptable composition, of polymer particles that are dispersed and surface-stabilized in a liquid fatty phase, to reduce or even eliminate marks, dyschromia, pigmentation defects, couperose and/or diffuse blood irrigations appearing across the skin, the said liquid fatty phase containing a volatile liquid phase and a non-volatile liquid phase, the non-volatile phase having a solubility parameter $\delta_h \leq 5$ $(J/cm^3)^{1/2}$ and the volatile phase/non-volatile phase weight ratio ranging from 2 to 25, the said composition containing a dyestuff.

Another preferred embodiment of the invention is also a process for the cosmetic care of the skin or for making up the skin, which includes applying to the skin a cosmetic composition as defined above.

Another preferred embodiment of the invention is also a non-therapeutic process (preferably a cosmetic process) for the camouflaging, preferably the remanent camouflaging, of marks, skin pigmentation defects, dyschromia, couperose, diffuse blood irrigations appearing across the skin and telangiectasias, this process including introducing, into a composition containing a dyestuff, a liquid fatty phase containing a volatile liquid phase, a non-volatile liquid phase and polymer particles that are dispersed and surface-stabilized in the liquid fatty phase, the non-volatile phase having a solubility parameter $\delta_h \leq 5$ $(J/cm^3)^{1/2}$ and the volatile phase/non-volatile phase weight ratio ranging from 2 to 25.

Preferably, the composition contains at least one ingredient chosen from cosmetic and dermatological active agents and mixtures thereof By virtue of the dispersion of surface-stabilized polymer particles present in the liquid fatty phase, the composition of the invention makes it possible to limit dr even eliminate the transfer of the composition and preferably the transfer of dyestuffs, and thus to keep these dyestuffs in the place where they were deposited, and to be resistant to water, sebum and sweat.

Polymer in Dispersion

According to the invention, the polymer is insoluble in the fatty phase even at its softening point, unlike a wax, even one of polymeric origin, which is soluble in the fatty phase at its melting point. It also makes it possible to form a film-forming deposit which is in the form of an isolable, continuous and homogeneous film and/or is characterized by the overlapping of the polymer chains. With a wax, even one obtained by polymerization, recrystallization is obtained after melting in the fatty phase.

The polymer used in the present patent application can be of any nature. It is thus possible to use a radical-mediated polymer, a polycondensate or even a polymer of natural origin and mixtures thereof. The polymer can be preferably chosen by a person skilled in the art as a function of its properties and depending on the subsequent use desired for the composition. Preferably, the polymer used is non-film-forming.

The expression "non-film-forming polymer" means a polymer not capable of forming, by itself, an isolable film. This polymer forms, in combination with the non-volatile phase, a continuous and homogeneous deposit on the skin.

Preferably, the polymer is in the form of particles that are dispersed and surface-stabilized. More preferably, the polymer is in the form of particles that are dispersed and surface-stabilized by at least one stabilizer.

One advantage of the use of a dispersion of particles in a composition of the invention is that the particles remain in the form of elementary particles, without forming aggregates, in the fatty phase, which would not be the case with nanometer-sized inorganic particles. Another advantage of the polymer dispersion is the possibility of obtaining very fluid compositions (of about 130 centipoises), even in the presence of a high polymer content.

Yet another advantage of such a dispersion is that it is possible to calibrate the size of the polymer particles as desired, and to modify their size "polydispersity" during synthesis. It is thus possible to obtain very small particles, which are invisible to the naked eye when they are in the composition and when they are applied to the skin. This would not be possible with pigments in particulate form, since the way in which they are made does not allow the average particle size to be modified.

It has moreover been observed that the compositions according to the invention have particularly advantageous spreading and adhesion qualities on the skin, as well as a pleasant, creamy feel. These compositions also have the advantage of being easy to remove, preferably with a standard make-up-removing milk. This is entirely remarkable since the compositions of the prior art with high transfer-resistance properties are very difficult to remove. In general, they are sold with a specific make-up-removing product, which places an additional constraint on the user.

The compositions according to the invention thus preferably include a stable dispersion of generally spherical particles of at least one polymer, in a physiologically acceptable liquid fatty phase. These dispersions can especially be in the form of polymer nanoparticles as a stable dispersion in the said fatty phase. The nanoparticles are preferably between 5 and 600 nm in size, given that beyond about 600 nm, the particle dispersions become much less stable. More preferably, the nanoparticles are between about 10 and 500 nm in size, more particularly preferably, between about 20 and 400 nm in size. These ranges include all values and subranges therebetween.

Yet another advantage of the polymer dispersion in the composition of the invention is the possibility of varying the glass transition temperature (Tg) of the polymer or of the polymeric system (polymer plus additive of the plasticizer type), and thus of going from a soft polymer to a relatively hard polymer, which allows the mechanical properties of the compositions to be adjusted as a function of the intended use. Modification of the glass transition temperature can be achieved preferably with one of the plasticizers usually used in the application fields concerned, and preferably from compounds capable of being solvents for the polymer.

The polymers which can be used in the composition of the invention preferably have a number-average molecular weight from about 2000 to 10,000,000 and a (Tg) from −100° C. to 300° C. and better still from −10° C. to 50° C. These ranges include all values and subranges therebetween.

When the polymer has a glass transition temperature that is too high for the desired use, it can be combined with a plasticizer so as to lower this temperature of the mixture used. The plasticizer can be chosen from the plasticizers usually used in the application field, and preferably from compounds capable of being solvents for the polymer.

Among the film-forming polymers which may be mentioned are acrylic or vinyl, radical-mediated homopolymers or copolymers, preferably having a Tg which is less than or equal to the temperature of the skin, and preferably less than or equal to 40° C. and more preferably ranging from −10° C. to 30° C. and most particularly preferably from −20° C. to 25° C. These ranges include all values and subranges therebetween.

Among the non-film-forming polymers which can be used in the invention, mention may be made of vinyl or acrylic, radical-mediated homopolymers or cop polymers, which are optionally crosslinked, preferably having a Tg of greater than or equal to 40° C. and more preferably ranging from 45 to 150° C. and most preferably from 50 to 125° C. These ranges include all values and subranges therebetween.

The expression "radical-mediated polymer" preferably means a polymer obtained by polymerization of monomers containing unsaturation, preferably ethylenic unsaturation, each monomer being capable of homopolymerizing (unlike polycondensates). The radical-mediated polymers can preferably be vinyl polymers or copolymers, preferably acrylic polymers.

The vinyl polymers can result from the polymerization of monomers containing ethylenic unsaturation and having at least one acid group and/or esters of these acidic monomers and/or amides of these acids.

As monomers bearing an acidic group, it is preferable to use $\alpha,\beta$-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The monomeric acid esters are preferably chosen from (meth)acrylic acid esters (also referred to as (meth) acrylates), such as alkyl (meth)acrylates, preferably of $C_1$–$C_{20}$, more preferably $C_1$–$C_8$, alkyl, aryl (meth)acrylates, preferably of $C_6$–$C_{10}$ aryl, and hydroxyalkyl (meth) acrylates, preferably of $C_2$–$C_6$ hydroxyalkyl. Alkyl (meth) acrylates which may be mentioned are methyl, ethyl, butyl, isobutyl, 2-ethylhexyl and lauryl (meth)acrylate. Hydroxyalkyl (meth)acrylates which may be mentioned are hydroxyethyl (meth)acrylate and 2-hydroxypropyl (meth)acrylate. Aryl (meth)acrylates which may be mentioned are benzyl or phenyl acrylates.

The (meth)acrylic acid esters which are particularly preferred are the alkyl (meth)acrylates.

Radical-mediated polymers which are preferably used are copolymers of (meth)acrylic acid and of alkyl (meth) acrylates, preferably of $C_1$–$C_4$ alkyl. More preferably, methyl acrylates optionally copolymerized with acrylic acid can be used.

Monomeric acid amides which may be mentioned are (meth)acrylamides, and especially N-alkyl(meth) acrylamides, preferably of $C_2$–$C_{12}$ alkyl, such as N-ethylacrylamide, N-t-butylacrylamide and N-octylacrylamide; N-di($C_1$–$C_4$)alkyl(meth)acrylamides.

The vinyl polymers can also result from the polymerization of monomers containing ethylenic unsaturation and having at least one amine group, in free form or else partially or totally neutralized, or alternatively partially or totally quaternized. Such monomers can be, for example, dimethylaminoethyl (meth)acrylate, dimethylaminoethylmethacrylamide, vinyl amine, vinylpyridine or diallyldimethylammonium chloride.

The vinyl polymers can also result from the homopolymerization or copolymerization of at least one monomer chosen from vinyl esters and styrene monomers. Preferably, these monomers can be polymerized with monomeric acids and/or their esters and/or their amides, such as those mentioned above. Examples of vinyl esters which may be mentioned are vinyl acetate, vinyl propionate, vinyl neodecanoate, vinyl pivalate, vinyl benzoate and vinyl t-butylbenzoate. Styrene monomers which may be mentioned are styrene and $\alpha$-methylstyrene.

The list of monomers given is not limiting and it is possible to use any monomer known to those skilled in the art which falls in the categories of acrylic and vinyl monomers (including monomers modified with a silicone chain).

Other vinyl monomers which may also be mentioned are:

N-vinylpyrrolidone, vinylcaprolactam, vinyl-N-($C_1$–$C_6$) alkylpyrroles, vinyloxazoles, vinylthiazoles, vinylpyrimidines and vinylimidazoles, olefins such as ethylene, propylene, butylene, isoprene and butadiene.

The vinyl polymer can be crosslinked using a difunctional monomer, preferably one including at least two ethylenic unsaturations, such as ethylene glycol dimethacrylate or diallyl phthalate.

Preferably, the polymers of the invention can be chosen from the following polymers or copolymers: polyurethanes, polyurethane-acrylics, polyureas, polyurea-polyurethanes, polyester-polyurethanes, polyether-polyurethanes, polyesters, polyesteramides, fatty-chain polyesters, alkyds; acrylic and/or vinyl polymers or copolymers; acrylic-silicone copolymers; polyacrylamides; silicone polymers, fluoro polymers and mixtures thereof.

Liquid Fatty Phase

The liquid fatty phase in which the polymer is dispersed can include any cosmetically or dermatologically acceptable oil, and more generally a physiologically acceptable oil, chosen preferably from oils of mineral, animal, plant or synthetic, carbon-based, hydrocarbon-based, fluoro and/or silicone origin, alone or as a mixture provided that they form a homogeneous, stable mixture and provided that they are compatible with the intended use, at least one of these oils having a solubility parameter $\delta_h \leq 5$. This oil or these oils of solubility parameter $\delta_h \leq 5$, which will be referred to as primary oils, are compatible with the dyestuff and the polymer particles, i.e., they preferably prevent any segregation of these polymer particles and of this dyestuff. These primary oils also make it possible to dissolve oils of solubility parameter $\delta_h \leq 5$, which are referred to as secondary oils, thus making these oils compatible with the polymer particles and the dyestuff.

Preferably, the solubility parameter of the primary oils is $\delta_h \leq 4$, and more preferably $\delta_h \leq 3$. These ranges include all values and subranges therebetween.

The definition of fatty substances in the three-dimensional solubility space according to Hansen is described in the article by C. M. Hansen: "The three dimensional solubility parameters" J. Paint Technol. 39, 105 (1967) and in the article "Solubility parameter values" by Eric A. Grulke from the book "Polymer Handbook" 3rd edition, Chapter VII, pages 519–559, the entire contents of each of which being hereby incorporated by reference.

According to this Hansen space: $\delta_h$ characterizes the specific interaction forces (such as hydrogen bonding, acid/base, donor/acceptor, etc. forces).

As non-volatile primary oils which can be used in the invention, mention may be made of a polar or slightly polar oils, i.e. oils including an alkyl chain, preferably a $C_3$–$C_{40}$ alkyl chain. Preferred examples of primary oils which may be mentioned are:

linear or branched hydrocarbons such as liquid paraffin, liquid petroleum jelly and light naphthalene oils, and lanolin;

hydrocarbon-based oils of animal origin such as squalene;

hydrocarbon-based plant oils such as liquid triglycerides of fatty acids containing from 4 to 10 carbon atoms, such as sunflower oil, olive oil, borage oil, corn oil, rice bran oil, wheatgerm oil, soybean oil, marrow oil, musk rose oil, blackcurrant pip oil, sesame oil, hazelnut oil, apricot oil, arara oil, macadamia oil, avocado oil, jojoba oil or refined oil of Limnanthes alba;

synthetic esters and ethers, preferably of fatty acids, such as oils of formula $R_1CO(O)_xR_2$ in which $R_1$ represents an acid residue including from 2 to 29 carbon atoms with x being 0 or 1 and $R_2$ represents a hydrocarbon-based chain containing from 3 to 30 carbon atoms, such as, for example, tributyl acetyl citrate, oleyl erucate, 2-octyldodecyl behenate, triisoarachidyl citrate, isocetyl or octyldodecyl stearoylstearate, n-propyl acetate, tridecyl trimellitate, diisocetyl dodecane di-oleate or stearate, arachidyl propionate, dibutyl phthalate, propylene carbonate, octyldodecyl pentanoate; polyol esters such as vitamin F, sorbitan isostearate, glyceryl or diglyceryl triisostearate;

silicone oils such as polydimethylsiloxanes (PDMS's), optionally including a $C_3$–$C_{40}$ alkyl or alkoxy chain or a phenyl chain, such as phenyltrimethicones, optionally fluorinated polyalkylmethylsiloxanes, such as polymethyltrifluoropropyldimethylsiloxanes, or with functional groups such as hydroxyl, thiol and/or amine groups; polysiloxanes modified with fatty acids, fatty alcohols or polyoxyalkylenes, fluorosilicones and perfluoro oils;

mixtures thereof.

Preferably, these non-volatile primary oils can represent from 1 to 15% of the total weight of the composition and better still from 5 to 10% and most preferably from 7 to 9%. These ranges include all values and subranges therebetween.

One or more secondary oils can optionally be added to these primary oils, these secondary oils being chosen from linear or branched hydrocarbons such as hydrogenated polyisobutylene; esters of fatty acids containing from 7 to 29 carbon atoms, such as diisostearyl malate, isopropyl palmitate, diisopropyl adipate, triglycerides of caprylic/capric acids such as those sold by the company Stearineries Dubois or those sold under the names Miglyol 810, 812 and 818 by the company Dynamit Nobel, liquid karite butter, isopropyl myristate, butyl stearate, hexyl laurate, diisopropyl adipate, isononyl isononate, 2-hexyldecyl laurate, 2-octyldecyl palmitate, 2-octyldodecyl myristate or lactate, 2-diethylhexyl succinate, 2-ethylhexyl palmitate, 2-octyldodecyl stearate, castor oil; esters of lanolic acid, of lauric acid or of stearic acid; higher fatty alcohols (containing from 7 to 29 carbon atoms) such as stearyl alcohol, linoleyl alcohol, linolenyl alcohol, isostearyl alcohol, 2-octyldodecanol, decanol, dodecanol, octadecanol or oleyl alcohol; higher fatty acids (containing from 7 to 29 carbon atoms) such as myristic acid, palmitic acid, stearic acid, behenic acid, oleic acid, linoleic acid, linolenic acid or isostearic acid; mixtures thereof.

Preferably, these secondary oils can represent from 0 to 10% of the total weight of the composition and better still from 0 to 5% and most preferably from greater than zero to 2.5%. These ranges include all values and subranges therebetween.

According to the invention, it is also possible to use one or more oils that are volatile at room temperature and atmospheric pressure. These volatile oils preferably make it easier to apply the composition to the skin. These oils can be hydrocarbon-based oils, silicone oils optionally including alkyl or alkoxy groups pendent or at the end of the silicone chain, or esters of acid and of lower alcohols ($C_1$ to $C_8$).

As volatile silicone oils which can be used in the invention, mention may be made of linear or cyclic silicones having a viscosity at room temperature of less than 8 cSt and preferably containing from 2 to 7 silicon atoms, these silicones optionally including alkyl or alkoxy groups containing from 1 to 10 carbon atoms. As volatile silicone oils which can be used in the invention, mention may be made preferably of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane, decamethyltetrasiloxane and mixtures thereof.

As other volatile oils which can be used in the invention, mention may be made preferably of $C_8$–$C_{16}$ isoalkane oils (also referred to as isoparaffins) such as isododecane, isodecane, isohexadecane and, for example, the oils sold under the trade names Isopar and Permetyl, and preferably isododecane (Permetyl 99 A), $C_8$–$C_{16}$ branched esters such as isohexyl neopentanoate, and mixtures thereof.

Preferably, one or more oils having a solubility parameter $\delta_h \leq 5$ are used as volatile oils, and preferably isododecane and $C_8$–$C_{16}$ isoparaffins.

These volatile oils represent preferably from 5 to 85% of the total weight of the composition and better still from 20 to 75% and most preferably from 30 to 50%. These ranges include all values and subranges therebetween.

The choice of the non-aqueous medium is made by a person skilled in the art as a function of the nature of the monomers constituting the polymer and/or of the nature of the stabilizer, as indicated below.

The polymer dispersion can be manufactured as described in document EP-A-749 747, the entire contents of which being hereby incorporated by reference. The polymerization can be carried out in dispersion, i.e. by precipitating the polymer during formation, with protection of the particles formed with a stabilizer.

A mixture including the initial monomers as well as a radical initiator is thus prepared. This mixture is dissolved in a solvent, which is referred to hereinbelow in the present description as the "synthesis solvent". When the fatty phase is a non-volatile oil, the polymerization can be carried out in an apolar organic solvent (synthesis solvent) followed by addition of the non-volatile oil (which should be miscible with the said synthesis solvent) and selective distillation of the synthesis solvent.

A synthesis solvent is thus chosen such that the initial monomers, and the radical initiator, are soluble therein, and the polymer particles obtained are soluble therein, in order for them to precipitate therefrom during their formation. Preferably, the synthesis solvent can be chosen from alkanes such as heptane, isododecane and cyclohexane.

When the fatty phase chosen contains a volatile oil, the polymerization can be carried out directly in the said oil, which also acts as synthesis solvent. The monomers should also be soluble therein, as should the radical initiator, and the polymer obtained should be insoluble therein.

The monomers are preferably present in the synthesis solvent, before polymerization, in a proportion of 5–20% by weight of the reaction mixture. All of the monomers can be present in the solvent before the start of the reaction, or some of the monomers may be added gradually as the polymerization reaction proceeds.

The radical initiator can be, preferably, azobisisobutyronitrile or tert-butylperoxy-2-ethyl hexanoate.

Stabilizer

The polymer particles are preferably surface-stabilized, as the polymerization proceeds, by means of a stabilizer which may be a block polymer, a grafted polymer and/or a random polymer, alone or as a mixture. The stabilization can be carried out by any known means, and preferably by direct addition of the block polymer, grafted polymer and/or random polymer during the polymerization.

The stabilizer is preferably also present in the mixture before polymerization. However, it is also possible to add it continuously, preferably when the monomers are also added continuously.

2–30% by weight of stabilizer relative to the initial mixture of monomers can be used, and preferably 5–20% by weight. These ranges include all values and subranges therebetween.

When a grafted polymer and/or block polymer is used as stabilizer, the synthesis solvent is chosen such that at least some of the grafts or blocks in the said stabilizing polymer are soluble in the said solvent, the other portion of the grafts or blocks not being soluble therein. The stabilizing polymer used during the polymerization should be soluble or dispersible in the synthesis solvent. Furthermore, a stabilizer is preferably chosen whose insoluble blocks or grafts have a certain affinity for the polymer formed during the polymerization.

Among the grafted polymers which may be mentioned are silicone polymers grafted with a hydrocarbon-based chain; hydrocarbon-based polymers grafted with a silicone chain.

Grafted copolymers having, for example, an insoluble skeleton of polyacrylic type with soluble grafts of poly-12-(hydroxystearic) acid type are also suitable for use.

Thus, block or grafted block copolymers including at least one block of polyorganosiloxane type and at least one block of a radical-mediated polymer can be used, such as grafted copolymers of acrylic/silicone type which can be used preferably when the non-aqueous medium is silicone-based.

It is also possible to use block or grafted block copolymers including at least one block of polyorganosiloxane type and at least one polyether. The polyorganopolysiloxane block can be, preferably, a polydimethylsiloxane or alternatively a poly($C_2$–$C_{18}$)-alkylmethylsiloxane; the polyether block can be a poly($C_2$–$C_{18}$)alkylene, preferably polyoxyethylene and/or polyoxypropylene. Preferably, it is possible to use dimethicone copolyols or ($C_2$–$C_{18}$)alkyldimethicone copolyols such as those sold under the name "Dow Corning 3225C" by the company Dow Corning, and lauryl methicones such as those sold under the name "Dow Corning Q2-5200" by the company "Dow Corning".

Block or grafted block copolymers which may also be mentioned are those including at least one block resulting from the polymerization of at least one ethylenic monomer containing one or more optionally conjugated ethylenic bonds such as ethylene or dienes such as butadiene and isoprene, and of at least one block of a vinyl polymer and better still a styrene polymer. When the ethylenic monomer includes several optionally conjugated ethylenic bonds, the residual ethylenic unsaturations after the polymerization are generally hydrogenated. Thus, in a known manner, the polymerization of isoprene leads, after hydrogenation, to the formation of ethylene/propylene block, and the polymerization of butadiene leads, after hydrogenation, to the formation of ethylene/butylene block. Among these polymers which may be mentioned are block copolymers, preferably of "diblock" or "triblock" type such as polystyrene/polyisoprene (SI), polystyrene/polybutadiene (SB) such as those sold under the name Luvitol HSB by BASF, of polystyrene/copoly(ethylene-propylene) type (SEP) such as those sold under the name Kraton by Shell Chemical Co. or alternatively of polystyrene/copoly(ethylene-butylene) type (SEB). Preferably, Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS) or Kraton D-1107 (SIS) can be used. The polymers are generally referred to as copolymers of hydrogenated or non-hydrogenated dienes.

Gelled Permethyl 99A-750, 99A-753-59 and 99A-753-58 (mixture of triblock polymer and starburst polymer), Versagel 5960 from Penreco (triblock polymer+starburst polymer); OS129880, OS129881 and OS84383 from Lubrizol (styrene/methacrylate copolymer) can also be used.

As block or grafted block copolymers including at least one block resulting from the polymerization of a monomer containing one or more ethylenic bonds such as dienes and at least one block of an acrylic polymer, mention may be made of poly(methyl methacrylate)/polyisobutylene diblock or triblock copolymers or grafted copolymers containing a poly(methyl methacrylate) skeleton and polyisobutylene grafts.

As block or grafted block copolymers including at least one block resulting from the polymerization of a monomer containing one or more ethylenic bonds and at least one block of a polyether such as a $C_2$–$C_{18}$ polyalkylene (preferably polyoxyethylenated and/or polyoxypropylenated), mention may be made of polyoxyethylene/polybutadiene or polyoxyethylene/polyisobutylene diblock or triblock copolymers.

When a random polymer is used as stabilizer, it is chosen such that it has a sufficient amount of groups making it soluble in the intended synthesis solvent.

It is thus possible to use copolymers based on alkyl acrylates or methacrylates derived from $C_1$–$C_4$ alcohols and alkyl acrylates or methacrylates derived from $C_8$–$C_{30}$ alcohols. Mention may be made preferably of the stearyl methacrylate/methyl methacrylate copolymer.

When the synthesis solvent is apolar, it is preferable to choose as stabilizer a polymer which gives the most complete coverage possible of the particles, several stabilizing polymer chains then being adsorbed onto a polymer particle obtained by polymerization.

In this case, it is preferred to use as stabilizer either a grafted polymer or a block polymer, so as to have better interfacial activity. The reason for this is that blocks or grafts which are insoluble in the synthesis solvent give a more voluminous coverage at the surface of the particles.

Moreover, when the liquid fatty phase includes at least one silicone oil, the stabilizer is preferably chosen from the group including of block or grafted block copolymers including at least one block of polyorganosiloxane type resulting from the polymerization of a siloxane and at least one block of a radical-mediated polymer or of a polyether or a polyester such as the polyoxypropylenated and/or oxyethylenated blocks.

When the liquid fatty phase includes no silicone oil, the stabilizer is preferably chosen from the group including:

(a) block or grafted block copolymers including at least one block of polyorganosiloxane type and at least one block of a radical-mediated polymer or of a polyether or a polyester, (b) copolymers of alkyl acrylates or methacrylates derived from $C_1$–$C_4$ alcohols, and of alkyl acrylates or methacrylates derived from $C_8$–$C_{30}$ alcohols, (c) block or grafted block copolymers including at least one block resulting from the polymerization of a monomer containing one or more ethylenic bonds such as dienes, and at least one block of a vinyl or acrylic polymer or of a polyether or a polyester, or mixtures thereof.

Preferably, diblock polymers are used as stabilizer.

The dispersions obtained can then be used in a composition, preferably a cosmetic or dermatological composition, such as a care or make-up composition for the skin which has camouflaging properties.

The composition preferably includes one or more dyestuffs containing one or more pulverulent compounds and/or one or more liposoluble dyes, for example in a proportion of from 0.01 to 70% of the total weight of the composition. The pulverulent compounds can be chosen from pigments and/or nacres. Furthermore, fillers such as those usually used in the fields considered can be provided.

Preferably, the pulverulent compounds represent from 0.1 to 30% of the total weight of the composition, preferably from 1 to 20% and better still from 1 to 10%. These ranges include all values and subranges therebetween. The more the amount of pulverulent compounds decreases, the more the transfer-resistance and comfort qualities increase. The fact that the transfer-resistance properties increase gradually as the amount of pulverulent compounds decreases is entirely surprising. The reason for this is that the transfer-resistance properties of the compositions of the prior art hitherto increased with the amount of pulverulent compounds. Conversely, their lack of comfort and their drying effect on the skin or mucous membranes increased.

Moreover, the transfer-resistance property increases with the amount of polymer dispersible in the liquid fatty phase. Preferably, the polymer can represent, as active material, up to 30% (as active or dry material) of the total weight of the composition. More preferably, the polymer represents up to 25%, most preferably up to 20%, and most particularly preferably up to 15% (as active or dry material) of the total weight of the composition. These ranges include all values and subranges therebetween. Using more than 12% by weight, of polymeric active material and of non-volatile oil, in the composition, a film which is totally transfer-resistant is obtained. Between 2% and 12%, the transfer-resistance effect is appreciable, although not total. The transfer-resistance properties can thus be adapted at will, which was not possible with the transfer-resistant compositions of the prior art, without having a detrimental effect on the level of comfort of the film deposited.

The pigments can be white or colored, inorganic and/or organic, and coated or uncoated. Among the inorganic pigments, mention may be made of titanium dioxide, which is optionally surface-treated, zirconium oxide or cerium oxide, as well as iron oxide or chromium oxide, manganese violet, ultramarine blue, chromium hydrate and ferric blue.

Among the organic pigments which may be mentioned are carbon black, pigments of D & C type and lakes based on cochineal carmine, barium, strontium, calcium or aluminum.

The nacreous pigments can be chosen from white nacreous pigments such as mica coated with titanium or with bismuth oxychloride, colored nacreous pigments such as titanium mica with iron oxides, titanium mica with, preferably, ferric blue or chromium oxide, titanium mica with an organic pigment of the abovementioned type and nacreous pigments based on bismuth oxychloride.

The fillers may be mineral or organic, and lamellar or spherical. Mention may be made of talc, mica, silica, kaolin, Nylon powder, poly-β-alanine powder and polyethylene powder, Teflon, lauroyllysine, starch, boron nitride, tetrafluoroethylene polymer powders, hollow microspheres such as Expancel (Nobel Industrie), Polytrap (Dow Corning) and silicone resin microbeads (for example Tospearls from Toshiba), precipitated calcium carbonate, magnesium hydrocarbonate and carbonate, hydroxyapatite, hollow silica microspheres (Silica Beads from Maprecos), glass or ceramic microcapsules, metal soaps derived from organic carboxylic acids containing from 8 to 22 carbon atoms, preferably from 12 to 18 carbon atoms, for example zinc, magnesium or lithium stearate, zinc laurate or magnesium myristate.

The liposoluble dyes are, for example, Sudan red, DC Red 17, DC Green 6, β-carotene, soybean oil, Sudan brown, DC Yellow 11, DC Violet 2, DC Orange 5 or quinoline yellow. They can represent from 0.01 to 20% of the weight of the composition and better still from 0.1 to 6%.

The polymer in the composition of the invention allows the formation of a film on the skin, forming a network which traps the dyestuffs (including the fillers) and/or the active agents. Depending on the relative amount of dyestuffs used, relative to the amount of stabilized polymer used, it is possible to obtain a film which is more or less shiny and more or less transfer-resistant.

Physiologically acceptable active agents (preferably cosmetic active agents) which may be mentioned are vitamins, essential fatty acids, sphingolipids, sunscreens, free-radical-scavenging active agents (preferably vitamin E), antipigmenting agents and keratolytic agents. These active agents are used in an amount which is usual for those skilled in the art, and preferably in concentrations of from 0.001 to 20% of the total weight of the composition.

Depending on the type of application envisaged, the composition according to the invention can moreover include the constituents conventionally used in the fields considered, which are present in an amount that is suitable for the desired pharmaceutical form.

Preferably, it can include, besides the liquid fatty phase in which the polymer is stabilized, additional fatty phases which can be chosen from waxes, gums and/or pasty fatty substances, of plant, animal, mineral, synthetic or even silicone origin, and mixtures thereof.

Among the waxes that are solid at room temperature, which may be present in the composition according to the invention, mention may be made of hydrocarbon-based waxes such as beeswax, carnauba wax, candelilla wax, ouricury wax, Japan wax, cork fibre waxes or sugar cane waxes, paraffin waxes, lignite waxes, microcrystalline waxes, lanolin wax, montan wax, ozokerites, polyethylene waxes, the waxes obtained by Fischer-Tropsch synthesis, hydrogenated oils, fatty esters and glycerides that are solid at 25° C. It is also possible to use silicone waxes, among which mention may be made of alkyl, alkoxy and/or esters of polymethylsiloxane. The waxes can be in the form of stable dispersions of colloidal particles of wax such that they can be prepared according to known methods, such as those in "Microemulsions Theory and Practice", L. M. Prince Ed., Academic Press (1977), pages 21–32, the entire contents of which being hereby incorporated by reference. As a wax which is liquid at room temperature, mention may be made of jojoba oil. Preferably, waxes with a melting point above 45° C. are used.

The waxes may be present in a proportion of 0–30% by weight in the composition, and better still from 0.5 to 10%. These ranges include all values and subranges therebetween.

The composition may also include any additive usually used in such compositions, such as thickeners, antioxidants, fragrances, preserving agents, liposoluble polymers such as polyalkylenes, preferably polybutene, polyacrylates and silicone polymers that are compatible with the fatty phase, as well as polyvinylpyrrolidone derivatives. Needless to say, a person skilled in the art will take care to select this or these optional additional compound(s), and/or the amount thereof, such that the advantageous properties of the composition according to the invention are not, or are not substantially, adversely affected by the addition envisaged.

In one especially embodiment of the invention, the compositions according to the invention can be prepared in a usual manner by a person skilled in the art. They can be in the form of a more or less fluid cream or gel, a more or less viscous paste or a solid anhydrous gel cast in a mold in the form of a dish or stick.

The composition of the invention can be a make-up product for the skin such as foundations, face powders, eyeshadows or make-up products for the body (semi-permanent tattoos). These products may also contain one or more cosmetic or dermatological active agents in order to give a care capacity to the make-up.

These compositions can preferably constitute a cosmetic or dermatological composition for protecting, treating or caring for the human face, neck, hands or body, and, for example, can constitute a care cream, an antisun product, an artificial tanning product or a dermatological ointment or salve.

EXAMPLES

Having generally described this invention, a farther understanding can be obtained by reference to certain specific examples which are provided herein for purposes of illustration only and are not intended to be limiting unless otherwise specified.

Example 1 of a Polymer Dispersion

A dispersion of polymethyl methacrylate crosslinked with ethylene glycol dimethacrylate, in isododecane, is prepared according to the method of Example 2 of document EP-A-749 746 (the entire contents of which being hereby incorporated by reference) replacing the Isopar L with isododecane. A dispersion of surface-stabilized polymethyl methacrylate particles in isododecane with a styrene/copoly (ethylene-propylene) diblock copolymer sold under the name Kraton G1701 (Shell), with a solids content of 19.7% by weight and an average particle size of 135 nm (polydispersity: 0.05) and a Tg of 100° C. is thus obtained. This copolymer is non-film-forming at room temperature.

Example 2 of a Foundation

The composition below is prepared:

| | |
|---|---|
| dispersion of Example 1: | 83 g |
| apricot kernel oil | 8 g |
| fillers (starch or talc) | 3.5 g |
| titanium oxide | 4 g |
| black iron oxide | 0.1 g |
| red iron oxide | 0.4 g |
| yellow iron oxide | 1 g |

This foundation is prepared in the following way: incorporation of the fatty substances and the pigments and fillers to obtain good dispersion of the fillers and pigments, followed by addition of the polymer dispersion, at room temperature (25° C.). The non-volatile oil used has a solubility parameter $\delta^h$ of 2.

This fluid foundation spreads well, is not sticky, not greasy, does not transfer and provides perfect camouflage for marks on the face and the hands.

A sensory test was carried out with this foundation by several experts; it was acknowledged as being comfortable to wear and as camouflaging marks perfectly. Its removal with a conventional make-up-removing product (Galateis from Lancome) was judged to be satisfactory, without leaving any traces.

Its remanence properties were tested in the following way: deposition of a thin coat (about 2 mg/cm$^2$) onto a Vitroskin substrate, soaking in tap water for 20 min at 28° C. After this soaking in hot water, foundation still remained. This foundation does indeed show water-remanence properties, allowing its use for the permanent camouflaging of marks on the hands.

In addition, this foundation is entirely stable over time, since no segregation is noted when it is placed in an oven for 2 months at 45° C. Similarly, after 3 years at room temperature (25° C.), no segregation is noted.

Obviously, numerous modifications and variations of the present invention are possible in light of the above teachings. It is therefore to be understood that within the scope of the appended claims, the invention may be practiced otherwise than as specifically described herein.

This application is based on French Patent Application No. 99 04815, filed on Apr. 16, 1999, the entire contents of which are hereby incorporated by reference.

What is claimed is:

1. An anhydrous composition for the skin, comprising:
   a liquid fatty phase comprising polymer particles that are dispersed and surface-stabilized therein, and
   a dyestuff, wherein
   said liquid fatty phase comprises a volatile liquid phase and a non-volatile liquid phase, the non-volatile phase having a solubility parameter $\delta_h \leq 5$ (J/cm$^3$)$^{1/2}$ and wherein a volatile phase/non-volatile phase weight ratio ranges from 2 to 25.

2. The composition according to claim 1, wherein said polymer particles are surface-stabilized by at least one stabilizer.

3. The composition according to claim 1, wherein said polymer particles comprise a polymer selected from the group consisting of radical-mediated polymers, polycondensate polymers, polymers of natural origin and mixtures thereof.

4. The composition according to claim 1, wherein said polymer particles comprise a polymer selected from the group consisting of polyurethanes, polyurethane-acrylics, polyureas, polyurea-polyurethanes, polyester-polyurethanes, polyether-polyurethanes, polyesters, polyesteramides, fatty-chain polyesters, alkyds, acrylic polymers, vinyl acrylic copolymers, acrylic copolymers, vinyl polymers, vinyl copolymers, acrylic-silicone copolymers, polyacrylamides, silicone polymers, fluoro polymers and mixtures thereof.

5. The composition according to claim 1, wherein said polymer particles comprise a non-film-forming polymer.

6. The composition according to claim 1, wherein the liquid fatty phase is an oil selected from the group consisting of mineral oil, animal oil, plant oil, synthetic oil, carbon-based oil, hydrocarbon-based oil, fluoro oil, fluorosilicone oil, silicone oil, and a mixture thereof, at least one of these oils having a solubility parameter $\delta_h \leq 5$ (J/cm$^3$)$^{1/2}$.

7. The composition according to claim 1, wherein said non-volatile liquid fatty phase is selected from the group consisting of:
   linear or branched hydrocarbons,
   hydrocarbon-based oils of animal origin,
   hydrocarbon-based plant oils
   liquid triglycerides of fatty acids containing from 4 to 10 carbon atoms,
   synthetic esters and ethers,
   synthetic esters and ethers, fatty acids,
   oils of formula $R_1CO(O)_xR_2$ in which $R_1$ represents an acid residue comprising from 2 to 29 carbon atoms and $R_2$ represents a hydrocarbon-based chain containing from 3 to 30 carbon atoms and x is 0 or 1,
   polyol esters,
   silicone oils,
   polysiloxanes modified with fatty acids, fatty alcohols or polyoxyalkylenes,
   fluorosilicones,
   perfluoro oils, and
   mixtures thereof.

8. The composition according to claim 1, wherein said non-volatile liquid fatty phase is selected from the group consisting of liquid paraffin, liquid petroleum jelly, light naphthalene oils, lanolin, squalene, sunflower oil, olive oil, borage oil, corn oil, rice bran oil, wheatgerm oil, soybean oil, marrow oil, musk rose oil, blackcurrant pip oil, sesame oil, hazelnut oil, apricot oil, arara oil, macadamia oil, avocado oil, jojoba oil or refined oil of Limnanthes alba, tributyl acetyl citrate, oleyl erucate, 2-octyldodecyl behenate, triisoarachidyl citrate, isocetyl or octyldodecyl stearoylstearate, n-propyl acetate, tridecyl trimellitate, diisocetyl dodecane di-oleate or stearate, arachidyl propionate, dibutyl phthalate, propylene carbonate, octyldodecyl pentanoate, vitamin F, sorbitan isostearate, glyceryl or diglyceryl triisostearate, phenyltrimethicones, optionally fluorinated polyalkylmethylsiloxanes, polymethyltrifluoropropyldimethylsiloxanes,
   polydimethylsiloxanes (PDMS's) comprising a $C_3$–$C_{40}$ alkyl or alkoxy chain or a phenyl chain, or comprising one or more functional groups, hydroxyl, thiol, amine groups, and mixtures thereof.

9. The composition according to claim 1, wherein the volatile phase/non-volatile phase weight ratio ranges from 5 to 15.

10. The composition according to claim 1, wherein said volatile liquid fatty phase comprises at least one oil selected from the group consisting of $C_8$–$C_{16}$ isoalkanes, $C_8$–$C_{16}$ branched esters and mixtures thereof.

11. The composition according to claim 1, wherein said non-volatile liquid fatty phase represents from 1 to 15% of the total weight of the composition.

12. The composition according to claim 1, wherein said polymer particles are dispersed and surface-stabilized by at least one stabilizer selected from the group consisting of block polymers, grafted polymers, random polymers and mixtures thereof.

13. The composition according to claim 1, wherein said polymer particles are dispersed and surface-stabilized by at least one said stabilizer is selected from the group consisting of silicone polymers grafted with a hydrocarbon-based chain; hydrocarbon-based polymers grafted with a silicone chain; copolymers grafted with an insoluble skeleton of polyacrylic type with soluble grafts of poly-12-(hydroxystearic) acid type; block or grafted block copolymers comprising at least one polyorgano-siloxane block and at least one block of a radical-mediated polymer; block or grafted block copolymers comprising at least one polyorganosiloxane block and at least one polyether; copolymers of $C_1$–$C_4$ alkyl acrylates or methacrylates, or of $C_8$–$C_{30}$ alkyl acrylates or methacrylates; block or grafted block copolymers comprising at least one block resulting from the polymerization of a monomer containing one or more ethylenic bonds and at least one block of a vinyl polymer; block or grafted block copolymers comprising at least one block resulting from the polymerization of a monomer containing one or more ethylenic bonds and at least one block of an acrylic polymer; block or grafted block copolymers comprising at least one block resulting from the polymerization of a monomer containing one or more ethylenic bonds and at least one block of a polyether, and mixtures thereof.

14. The composition according to claim 1, wherein said polymer particles are dispersed and surface-stabilized by at least one stabilizer, and wherein said stabilizer is a block or grafted block polymer comprising at least one block resulting from the polymerization of a monomer containing one or more ethylenic bonds and at least one block of a vinyl polymer, or comprising a polyoxypropylenated and/or oxyethylenated block and a block resulting from the polymerization of a siloxane.

15. The composition according to claim 1, further comprising at least one additional fatty phase selected from the group consisting of waxes, gums and/or pasty fatty substances of plant, animal, mineral, synthetic or silicone origin, and mixtures thereof.

16. The composition according to claim 1, wherein said dyestuff comprises at least one pulverulent compound selected from the group consisting of pigments, nacres, lipophilic dyes, and mixtures thereof.

17. The composition according to claim 16, wherein said pulverulent compound represents up to 30% of the total weight of the composition.

18. The composition according to claim 1, further comprising at least one filler.

19. The composition according to claim 1, wherein said polymer particles represent, as solids, up to 30% of the total weight of the composition.

20. The composition according to claim 1, which is in the form of an anhydrous gel, a skin care product, a make-up product for the skin, a foundation, a face powder, an eyeshadow, a care cream or protective cream for the skin, a care product or make-up product for the body, an antisun cream or a product for artificially tanning the skin, and combinations thereof.

21. The composition according to claim 1, further comprising at least one cosmetic or dermatological active agent.

22. A method of reducing or eliminating eliminate marks, dyschromia, pigmentation defects, couperose and/or diffuse blood irrigations appearing across the skin, comprising applying to the skin an anhydrous composition for the skin, comprising:

a liquid fatty phase comprising polymer particles that are dispersed and surface-stabilized therein, and a dyestuff, wherein said liquid fatty phase comprises a volatile liquid phase and a non-volatile liquid phase, the non-volatile phase having a solubility parameter $\delta_h \leq 5$ $(J/cm^3)^{1/2}$ and wherein a volatile phase/non-volatile phase weight ratio ranges from 2 to 25.

23. A non-therapeutic or cosmetic process for the camouflaging and/or the remanent camouflaging of marks, skin pigmentation defects, dyschromia, couperose, diffuse blood irrigations appearing across the skin and telangiectasias, comprising applying to the skin an anhydrous composition for the skin, comprising:

a liquid fatty phase comprising polymer particles that are dispersed and surface-stabilized therein, and a dyestuff, wherein said liquid fatty phase comprises a volatile liquid phase and a non-volatile liquid phase, the non-volatile phase having a solubility parameter $\delta_h \leq 5$ $(J/cm^3)^{1/2}$ and wherein a volatile phase/non-volatile phase weight ratio ranges from 2 to 25.

* * * * *